US009242097B2

(12) United States Patent
Mokelke et al.

(10) Patent No.: US 9,242,097 B2
(45) Date of Patent: Jan. 26, 2016

(54) SYSTEM AND METHOD FOR MAPPING BARORECEPTORS

(71) Applicant: Cardiac Pacemakers, Inc., St. Paul, MN (US)

(72) Inventors: Eric A. Mokelke, White Bear Lake, MN (US); Eric Falbe Hammill, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/307,209

(22) Filed: Jun. 17, 2014

(65) Prior Publication Data
US 2014/0371810 A1  Dec. 18, 2014

Related U.S. Application Data

(60) Provisional application No. 61/836,431, filed on Jun. 18, 2013.

(51) Int. Cl.
| | |
|---|---|
| *A61N 1/00* | (2006.01) |
| *A61N 1/36* | (2006.01) |
| *A61N 1/05* | (2006.01) |
| *A61B 5/021* | (2006.01) |
| *A61B 5/024* | (2006.01) |
| *A61B 5/08* | (2006.01) |

(52) U.S. Cl.
CPC .............. *A61N 1/36185* (2013.01); *A61N 1/05* (2013.01); *A61N 1/36117* (2013.01); *A61N 1/36139* (2013.01); *A61B 5/021* (2013.01); *A61B 5/024* (2013.01); *A61B 5/08* (2013.01); *A61N 1/0553* (2013.01)

(58) Field of Classification Search
CPC ....... A61N 1/36185; A61N 1/05; A61N 1/08; A61N 1/36128; A61N 1/36135; A61N 1/36139
See application file for complete search history.

(56) References Cited

U.S. PATENT DOCUMENTS

| | | | |
|---|---|---|---|
| 7,499,742 | B2 | 3/2009 | Bolea et al. |
| 7,509,166 | B2 | 3/2009 | Libbus |

(Continued)

FOREIGN PATENT DOCUMENTS

WO  WO-2014204980 A1  12/2014

OTHER PUBLICATIONS

"International Application Serial No. PCT/US2014/042770, International Search Report mailed Oct. 10, 2014", 4 pgs.

(Continued)

*Primary Examiner* — Robert N Wieland
(74) *Attorney, Agent, or Firm* — Schwegman Lundberg & Woessner, P.A.

(57) ABSTRACT

An example of a method embodiment may place a set of stimulation electrodes on tissue containing the baroreceptor region, and may test bipolar configurations of the electrodes. Each of the bipolar configurations of the electrodes includes at least one of the electrodes configured to function as an anode and at least one other of the electrodes configured to function as a cathode. Testing the bipolar configurations may include stimulating the tissue using each of the bipolar configurations. For each of the tested bipolar configurations at least one physiological parameter may be monitored for a baroreflex response to stimulation of the tissue, and the baroreflex response may be recorded for each of the tested bipolar configurations.

20 Claims, 13 Drawing Sheets

(56) References Cited

U.S. PATENT DOCUMENTS

| | | |
|---|---|---|
| 7,747,323 B2 | 6/2010 | Libbus et al. |
| 7,869,881 B2 | 1/2011 | Libbus et al. |
| 7,894,895 B2 | 2/2011 | Libbus et al. |
| 7,949,400 B2 | 5/2011 | Kieval et al. |
| 8,041,423 B2 | 10/2011 | Libbus et al. |
| 8,116,873 B2 | 2/2012 | Anderson et al. |
| 8,131,359 B2 | 3/2012 | Libbus et al. |
| 8,131,373 B2 | 3/2012 | Libbus |
| 8,195,289 B2 | 6/2012 | Heil, Jr. et al. |
| 8,214,050 B2 | 7/2012 | Kieval |
| 8,249,705 B1 | 8/2012 | Kieval et al. |
| 8,249,711 B2 | 8/2012 | Libbus et al. |
| 8,290,595 B2 | 10/2012 | Kieval et al. |
| 8,321,023 B2 | 11/2012 | Libbus et al. |
| 8,401,653 B2 | 3/2013 | Libbus et al. |
| 8,401,672 B2 | 3/2013 | Libbus et al. |
| 8,437,867 B2 | 5/2013 | Murney et al. |
| 8,442,638 B2 | 5/2013 | Libbus et al. |
| 8,442,640 B2 | 5/2013 | Libbus |
| 8,457,734 B2 | 6/2013 | Libbus et al. |
| 8,560,076 B2 | 10/2013 | Kieval et al. |
| 8,606,359 B2 | 12/2013 | Rossing et al. |
| 8,626,282 B2 | 1/2014 | Libbus et al. |
| 8,626,301 B2 | 1/2014 | Libbus |
| 8,682,430 B2 | 3/2014 | Libbus et al. |
| 8,682,434 B2 | 3/2014 | Libbus |
| 8,694,104 B2 | 4/2014 | Libbus et al. |
| 2003/0060848 A1 | 3/2003 | Kieval et al. |
| 2006/0004417 A1 | 1/2006 | Rossing et al. |
| 2007/0156201 A1 | 7/2007 | Rossing |
| 2008/0082137 A1 | 4/2008 | Kieval et al. |
| 2008/0154349 A1 | 6/2008 | Rossing et al. |
| 2012/0029600 A1* | 2/2012 | Zhou et al. ............. 607/62 |
| 2012/0109250 A1 | 5/2012 | Cates et al. |
| 2012/0232613 A1* | 9/2012 | Kieval et al. ........... 607/44 |
| 2012/0271389 A1 | 10/2012 | Cates et al. |
| 2013/0090700 A1* | 4/2013 | Kieval et al. ........... 607/3 |
| 2014/0128708 A1 | 5/2014 | Kieval |

OTHER PUBLICATIONS

"International Application Serial No. PCT/US2014/042770, Written Opinion mailed Oct. 10, 2014", 8 pgs.

\* cited by examiner

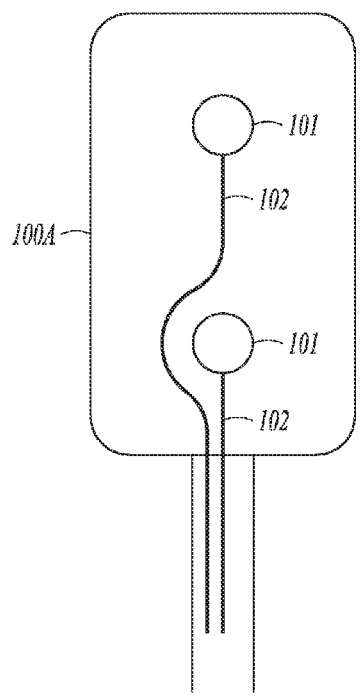
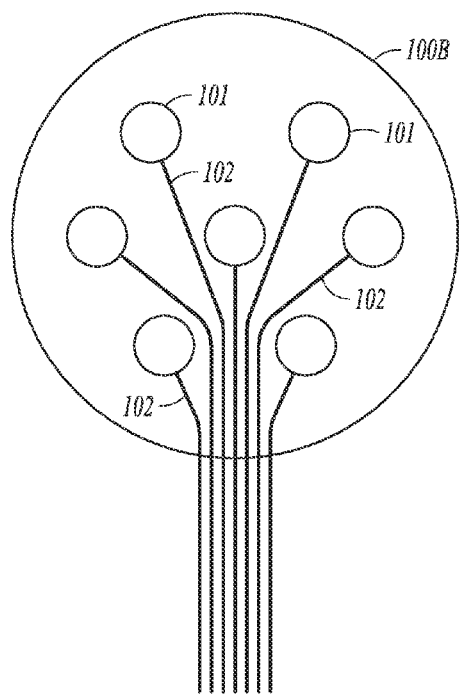
FIG. 1A    FIG. 1B
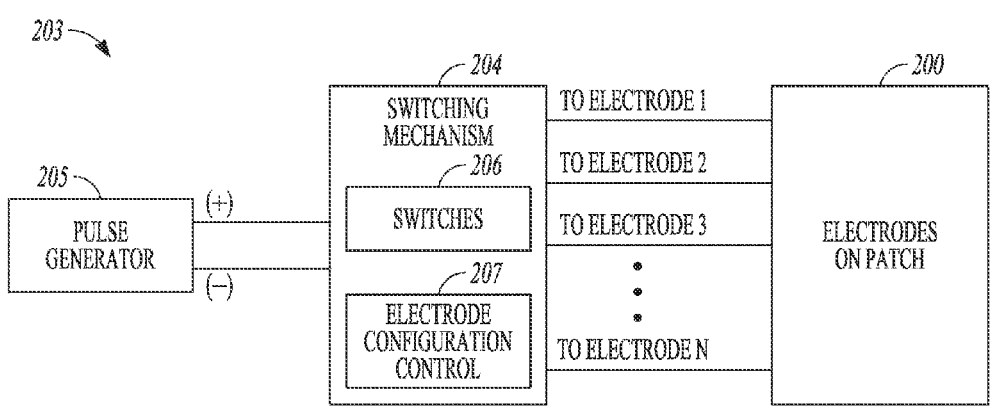
FIG. 2

| ELECTRODE | A | RETURN | Z | ΔMAP |
|---|---|---|---|---|
| E4  (+) | 3mA | E1 (−) |  | -16 |
| E4  (+) | 3mA | E2 (−) |  | -17 |
| E4  (+) | 3mA | E3 (−) |  | -13 |

○ E4
○ E3
○ E2
○ E1

| A4 | -15 | -17 | -15 | -13 |
| A3 | -7 | -12 | -19 | -13 |
| A2 | -6 | -10 | -17 | -9 |
| A1 | -9 | -11 | -15 | -15 |
|  | C1 | C2 | C3 | C4 |

SYSTEM AND METHOD FOR MAPPING BAROVECEPTORS

CLAIM OF PRIORITY

This application claims the benefit of priority under 35 U.S.C. §119(e) of U.S. Provisional Patent Application Ser. No. 61/836,431, filed on Jun. 18, 2013, which is herein incorporated by reference in its entirety.

TECHNICAL FIELD

This document relates generally to medical devices, and more particularly, to systems, devices and methods for delivering electrical stimulation.

BACKGROUND

Neural stimulation has been proposed as a therapy to treat high blood pressure. For example, it has been proposed that electrical stimulation can be used to reduce blood pressure when the electrical stimulation is directed at the baroreceptor regions to induce a baroreflex response. Baroreceptors play an important role in regulating blood pressure, and are located throughout the body, but primarily in the arch of the aorta and the carotid sinuses of the left and right internal carotid arteries. Through a negative feedback baroreflex system, the central nervous system can regulate the BP to maintain the blood pressure at a relatively stable level. For example, arterial pressure that causes stretch triggers the baroreflex to send nerve impulses to the brain which responds by controlling the pumping activity of the heart and blood vessel dilation to reduce the blood pressure.

The blood pressure response can fluctuate dramatically when different areas of the baroreceptor region are stimulated. For example, the blood pressure response at a first site within the baroreceptor region can be significantly different than the blood pressure response at a second site within the baroreceptor region. Animal experiments indicate responses can dramatically fluctuate spatially within 1 mm. Experience with humans also show focal distribution. Thus, the implantation of a baromodulation device to stimulate a small baroreceptor region in the carotid sinus usually requires extensive mapping of the internal carotid arteries in order to find a desirable stimulation location along the carotid artery that provides an effective or an apparently most effective control of blood pressure. Currently, surgeons manually hold one or more electrode(s) at various locations near the carotid sinus to map the baroreceptor region during an implantation procedure. Mapping may take up to several hours. This procedure takes significant time and effort due to the difficulty of manually positioning the electrode and maintaining steady and consistent blood pressure. Longer procedure times also undesirably expose the patient to longer anesthesia times. Thus, the clinical procedure is often unable to access a full mapping area. Moreover, the manual operation may cause trauma, or introduce mechanical activation of the baroreceptors which may hinder the evaluation of the blood pressure responses to the electrical stimulation.

SUMMARY

Various embodiments described methods and systems for mapping baroreceptor regions. An example of a method embodiment may place a set of stimulation electrodes on tissue containing the baroreceptor region, and may test bipolar configurations of the electrodes. Each of the bipolar configurations of the electrodes includes at least one of the electrodes configured to function as an anode and at least one other of the electrodes configured to function as a cathode. Testing the bipolar configurations may include stimulating the tissue using each of the bipolar configurations. For each of the tested bipolar configurations at least one physiological parameter may be monitored for a baroreflex response to stimulation of the tissue, and the baroreflex response may be recorded for each of the tested bipolar configurations.

An example of a method for mapping a baroreceptor region may include placing a set of stimulation electrodes on tissue containing the baroreceptor region and mapping one or more cathode clusters to confirm at least one of the cathode cluster is proximate to a baroreceptor hotspot. Each of the cathode clusters may include three or more of the stimulation electrodes connected to function as a cathode and wherein at least one other of the stimulation electrodes is connected to function as an anode. For each cathode cluster confirmed to be proximate to the baroreceptor hotspot, the method may conduct a secondary mapping to test at least two smaller cathode clusters to confirm at least one of the smaller cathode clusters is proximate to the baroreceptor hotspot. For each smaller cathode cluster confirmed to be proximate to the baroreceptor hotspot, the method may include mapping individual cathode electrodes within the smaller cathode duster to confirm at least one of the individual cathode electrodes is proximate to the baroreceptor hotspot.

An example of a system for mapping a baroreceptor region may include stimulation electrodes, a stimulator, at least on physiologic response sensor. The stimulator may include a stimulation controller, a pulse generator, and switches, and the stimulation controller and switches may be configured to connect different combination of the stimulation electrodes to the pulse generator to deliver bipolar stimulation of the tissue. The physiologic response sensor(s) may be configured to sense a physiologic response to stimulation of the tissue. The controller may include a stimulation protocol selector configured to select electrode configurations for testing, where the controller may be configured to control the switches to connect the pulse generate to the stimulation electrodes to provide selected electrode configurations for testing. The controller may include a physiologic feedback module to receive a signal from the at least one sensor, and a physiologic parameter analyzer configured to monitor a baroreflex response. The controller may be configured to use the stimulation protocol selector and the physiologic feedback module to map the baroreceptor region. In mapping the baroreceptor region, the controller may be configured to: stimulate the tissue using bipolar configurations of the electrodes to test the bipolar configurations, each of the bipolar configurations of the electrodes including at least one of the electrodes functioning as an anode and at least one other of the electrodes functioning as a cathode, for each of the tested bipolar configurations monitor at least one physiological parameter for a baroreflex response to stimulation of the tissue, and record the baroreflex response for each of the tested bipolar configurations.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 1A and 1B illustrate lead examples with more than one electrode that can be used to deliver bipolar stimulation to a baroreceptor field.

FIG. 2 illustrates an example of a system capable of connecting electrodes on the patch as cathodes and capable of connecting electrodes on the patch as anodes.

DETAILED DESCRIPTION

Figure 3:
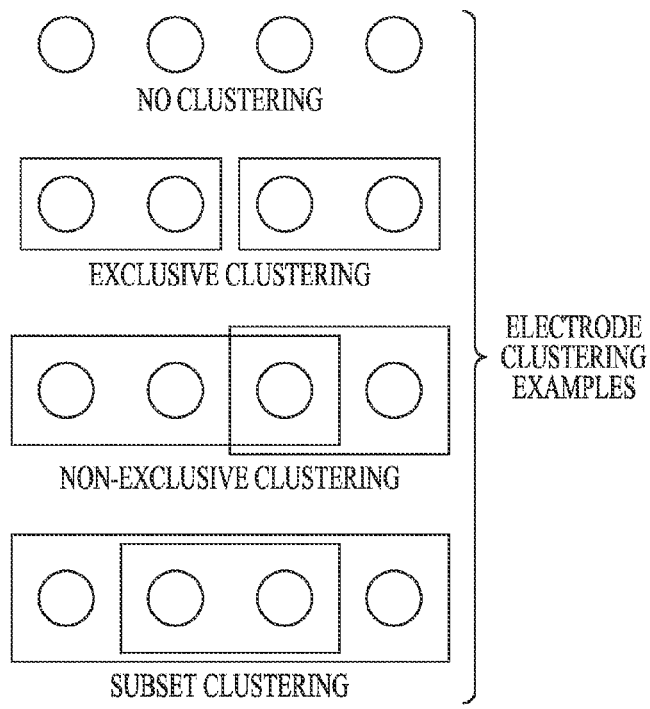
FIG. 3 illustrates examples for clustering electrodes together for connection as an anode or tier connection as a cathode.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Disclosed herein are systems, devices and methods for stimulating a baroreceptor region. For example, various embodiments described herein improve the process for mapping the baroreceptor region, which can be used for identifying a baroreceptor hotspot. Some embodiments, by way of example, provide a lead with a multitude of electrodes for electrically stimulating vascular tissue including the carotid sinus, which is positioned once on the target tissue and an algorithm for systematically stimulating one or more of the electrodes for detection of the target location. Various embodiments provide a multi-electrode patch capable of multiple bipolar stimulation configurations, which can be used to electronically reposition the bipolar stimulation field to stimulate the identified hot spot. The patch may also be used to provide unipolar stimulation, where the anode is provided by a can electrode on the implantable device housing. By way of example, circular electrodes may be attached to lead cables and imbedded within the area of a specific backing material that can be individually assigned as a cathode or anode with the control system. The greatest hemodynamic response may be provided by using a bipolar stimulation configuration where the cathode is near or placed over the baroreceptor hotspot. The use of a bipolar stimulation limits the stimulation field, and thus is less susceptible to undesirable extraneous muscle/nerve stimulation and is less susceptible to be sensed by another implantable device.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. The ANS may function in an involuntary, reflexive manner to regulate glands, to regulate muscles in the skin, eye, stomach, intestines and bladder, and to regulate cardiac muscle and the muscle around blood vessels, for example. The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. The heart rate and force is increased when the sympathetic nervous system is stimulated, and is decreased when the sympathetic nervous system is inhibited and the parasympathetic nervous system is stimulated. Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system and/or inhibiting the sympathetic nervous system constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems.

A pressoreceptive region or field is capable of sensing changes in pressure, such as changes in blood pressure. Pressoreceptor regions are referred to herein as baroreceptors. Baroreceptors are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activates baroreceptors in the vessel walls. Activation of baroreceptors naturally occurs through internal pressure and stretching of the arterial wall, which excites the parasympathetic nervous system causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance. Centrally mediated reflex pathways modulate cardiac rate, contractility and excitability.

Baroreflex is a reflex triggered by stimulation of a baroreceptor. Stimulating a baroreflex pathway and/or baroreceptors inhibits sympathetic nerve activity, stimulates the parasympathetic nervous system and reduces systemic arterial pressure by decreasing peripheral vascular resistance and cardiac contractility. Baroreceptor areas may be electrically stimulated to induce a baroreflex. As used herein, electrically stimulating a baroreceptor includes stimulating the nerve tissue including the nerve endings that innervate the baroreceptors. Stimulation of this nerve tissue near the baroreceptors causes neural signals to be sent to the central nervous system and induces a baroreflex response.

Baroreflex stimulation has been proposed for various therapies, including hypertension therapy and heart failure therapy. Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease. Other therapies have been proposed as well, such as therapies to treat arrhythmias.

Baroreceptor distribution may vary from person-to-person. However, baroreceptors appear to be more highly concentrated near the bifurcation of the interior carotid artery (ICA) and external carotid artery (ECA) off of the common carotid artery (CCA). Thus, some embodiments provide an orientation to stimulate the tissue area with the high concentration of baroreceptors.

Modeling information suggests that it is the tissue directly under the cathode that gets the greatest amount of energy. Thus, locating the cathode of the stimulation near a baroreceptor hotspot is desirable. The location of the anode appears to be less significant, and can be positioned away from potential cathodes for the stimulation configuration. However, placing the anode under the shielding of the backing mitigates extraneous stimulation. The backing can follow the contour of the electrodes so that there is a minimum of backing extending from the edge of each electrode.

Some embodiments use an accelerometer as part of mapping algorithm because the mapping electrode can be temporarily attached to the carotid sinus and the mapping algorithm can be automatically run to track the baroreflex response while evaluating extraneous stimulation using an accelerometer that serves as a sensitive sensor of motion.

Additionally, the use of a multi-electrode lead provides desirable redundancy. For example, another stimulation protocol, including bipolar or unipolar stimulations, may be selected if there is a problem with the electrode configuration used to deliver therapy.

FIGS. 1A and 1B illustrate lead examples with more than one electrode that can be used to deliver bipolar stimulation to a baroreceptor field. Each of these lead examples includes backing material which is also referred to herein as a patch 100A and 100B. A pattern of two or more electrodes 101 is positioned on a side of patch. The patch is constructed of material that may be implanted within the patient and may be sutured or otherwise attached to tissue near the carotid sinus. The patch is pliable, allowing the patch to generally conform to the surface of the tissue to which it is attached. The patch may act as a shield to keep electrical stimulation fields on the electrode side of patch. Each electrode 101 may be connected to a respective wire 102, which allows any of the electrodes to be selectively used in delivering the bipolar stimulation to tissue in the carotid sinus. Each wire may extend from the electrode near a distal end of the lead toward a proximal end of the lead. In some embodiments, a multiplexor may be used near the distal end of the lead so that fewer conductors need be used in the lead. In some embodiments, some of the electrodes may be electrically connected together (e.g. hard wired) which also would also only require fewer wires in the lead. It is noted that these electrode patterns are examples, and are not intended to be exclusive examples. Rather, the bipolar stimulation configuration can be selected to use a selected one or more of the electrodes as a cathode. In some embodiments, the bipolar stimulation configuration can be selected to use a selected one or more of the electrodes as an anode.

FIG. 2 illustrates an example of a system capable of connecting electrodes on the patch as cathodes and capable of connecting electrodes on the patch as anodes. The illustrated system 203 may include electrodes on a patch 200, such as illustrated in 100A or 100B or such another patch with two or more electrodes. The system 203 also includes a switching mechanism 204 configured to connect electrode(s) as cathode electrodes for bipolar stimulation. FIG. 2 also illustrates a pulse generator 205 configured to deliver electrical neural stimulation using two conductors, labeled in the figure as "(+)" for use to connect to an anode and "(−)" for use to connect to a cathode. The switching mechanism 204 includes switches 206 and an electrode configuration control 207 configured to control the switches to select the electrode(s) to function as the cathode for bipolar stimulation. For example, the switching mechanism 204 may be capable of electrically connecting a first and/or a second electrode to the (−) output of the pulse generator 205. In some embodiments, the switching mechanism 204 may also be configured to control the switches to select the electrode(s) to function as an anode for the bipolar stimulation, connecting those selected electrode(s) to the (+) output of the pulse generator. In some embodiments, the anode is directly connected to the (+) output of the pulse generator.

FIG. 3 illustrates examples for clustering electrodes together for connection as an anode or for connection as a cathode. The first example 208 illustrates four electrodes that are not clustered together. The second example 209 illustrates the four electrodes clustered into separate clusters where the electrodes in one cluster are exclusive from the electrodes in the other cluster. That is, the clusters may be exclusive groupings. The third example illustrates the four electrodes clustered into two clusters, but where the electrodes in the clusters are non-exclusive. That is, both electrodes may share one or more electrodes, but also include an electrode that is not found in the other cluster. In other words, the clusters may be non-exclusive groupings. The fourth example illustrates the four electrodes clustered into two clusters, where one cluster is a subset of the other cluster. In other words, one cluster may be a subset of another cluster. Thus, the system can be configured to cluster the electrodes in a variety of ways, including exclusive clusters, non-exclusive clusters, and subset clusters. The system can be configured to disassemble the clusters into smaller clusters or into the individual electrodes, and then use these smaller clusters or individual electrodes to create other clusters. FIG. 3 has illustrated exclusive, non-exclusive, and subset clusters using a set of four electrodes. However, the present subject matter is not limited to a set of four electrodes.

Figure 4:
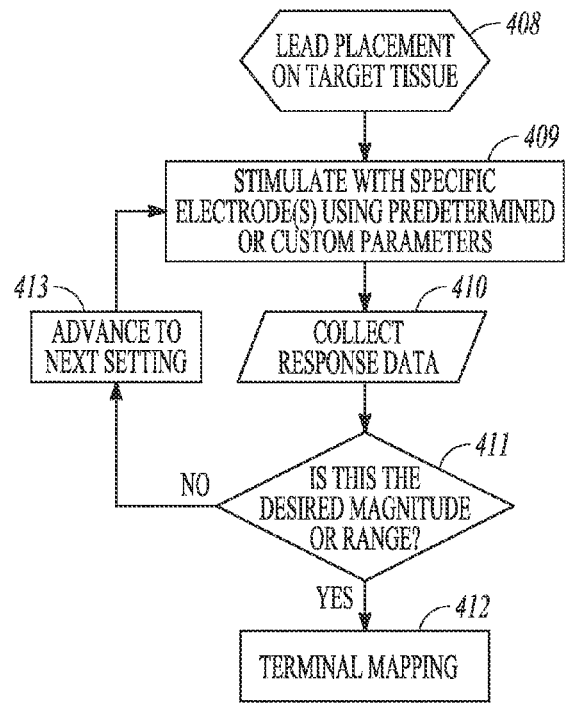
FIG. 4 illustrates an example of a method for mapping a baroreceptor region.

FIG. 4 illustrates an example of a method for mapping a baroreceptor region. In the illustrated example, a lead is placed against target tissue at 408. For example, this tissue may be tissue near the carotid sinus where baroreceptors are located. The mapping process is performed with the lead placed on the target tissue. Specific electrode(s) are stimulated using predetermined or custom parameters at 409, and response data is collected at 410. The response to stimulating baroreceptors can be referred to as a baroreflex response. Examples of parameters that may be sensed to detect a baroreflex response may include, but are not limited to, heart rate, blood pressure, and/or respiration. At 411, it is determined whether the baroreflex response is within a desired magnitude or range. If the baroreflex response is desired, then the mapping is terminated 412. If the baroreflex response is not desired, then the mapping process advances to the next setting at 413, and electrode(s) are stimulated at 409.

Figure 5:
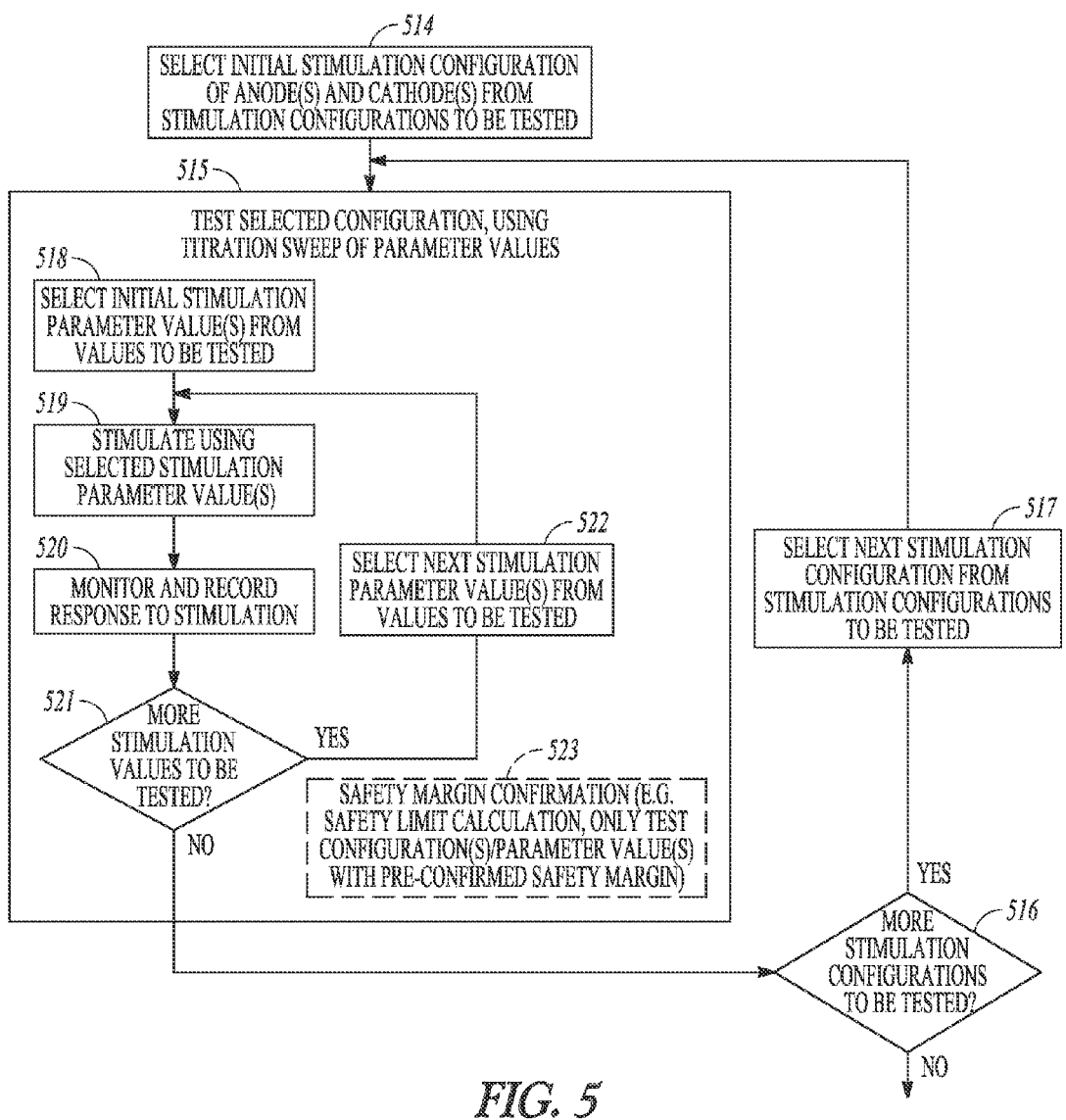
FIG. 5 illustrates an example of a method for mapping a baroreceptor region.

FIG. 5 illustrates an example of a method for mapping a baroreceptor region. The illustrated method is performed after attaching electrodes to tissue near the baroreceptor region. At 514, an initial stimulation configuration of anode(s) and cathode(s) is selected from a set of stimulation configurations to be tested. A mapping system, for example, may be configured to test a group of stimulation configurations. The selected configuration is tested at 515. If more stimulation configurations are to be tested 516, then the next stimulation configuration is tested from the set of stimulation configurations to be tested 517. In some embodiments, the testing of the selected configuration 515 may use a titration sweep of parameter values. These stimulation parameter values may include one or more of amplitude, pulse width, pulse frequency, burst duration for a train of pulses, burst cycle duration, and a duty cycle (e.g., burst duration/burst cycle duration). For example, the initial stimulation parameter value may be selected from a set of stimulation values to be tested 518. The selected stimulation parameter values are used to stimulate the tissue 519. The response to the stimulation is monitored and recorded 520. This response may be referred to as a baroreflex response. By way of example and not limitation, heart rate, blood pressure or respiration may be used to sense a baroreflex response to stimulating baroreceptors. If more stimulation values are to be tested for the stimulation configuration 521, then process proceeds to 522 to select the next stimulation parameter value(s) from the set of stimulation values to be tested.

Some embodiments may provide safety margin confirmation 523. For example, the safety margin configuration may be a safety limit calculation. The safety margin configuration may involve pre-confirming the safety margin to confirm that any test values for a configuration have an appropriate safety margin. U.S. Pub. No. 2011/0313488, entitled Automatic Neural Stimulation Titration Sweep discuss a titration sweep used to select parameters that provide an efficacious neural stimulation and that also provide a desirable safety margin to prevent injury to tissue. U.S. Pub. No. 2011/0313488 is incorporated by reference herein it is entirety. A brief discussion of neural safety follows.

Nerve recruitment, effectiveness and neural safety depend on charge delivered and charge density (current amp×pulse width/electrode area). Safety and patient tolerance for the therapy limit the charge density that can be delivered. Prolonged neural stimulation can cause damage in the peripheral/central nervous system, and electrode-induced neural damage is a concern as the therapy should be delivered in a safe manner. The amount of charge that can be injected into neural tissue without causing harm ("safety limit") has been referred to as the charge injection limit or charge density limit. Studies have been performed in several animal models to help establish neural stimulation safety limits for neural stimulation. Systems may be designed to provide a safety margin from these safety limits.

The charge per phase and charge density per phase are important parameters for neural stimulation-induced damage. Charge density per phase and charge per phase are related to current density and total injected current respectively. Charge per phase (Q) is the total volume within which the neurons are excited and is measured in C/phase. Where is electrical current amplitude and I is time the current was delivered, the charge per phase (Q) can be expressed as:

$$Q=It$$

Charge density per phase (QD) determines the proportion of neurons close to an electrode that are excited. The charge density per phase (QD) can be calculated as the ratio of the charge per phase to the surface area of the electrode (coulomb/area-phase):

$$QD=It SA.$$

This equation calculates average charge density. It has been reported that there is charge accumulation near the edges of the interface between the electrode and tissue. Charge density is a function of several variables, including the amount of current delivered, the surface area of the stimulating electrode, and the pulse width. Charge density (QD) can be expressed with the units "microcoulombs/cm$^2$/phase."

Figures 6, 7:
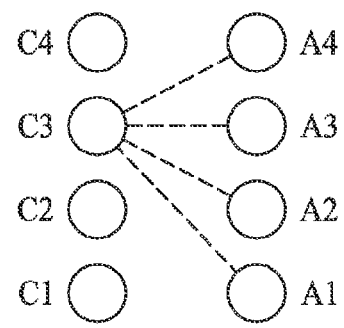
FIG. 6 illustrates an example of baroreflex response results for testing various bipolar stimulation configuration using electrode E4 as an anode and testing each of electrodes E1-E3 as a cathode.
FIG. 7 illustrates an example of baroreflex response results for testing various bipolar stimulation configuration using each of electrodes C1-C4 as a cathode and using each one of electrodes A1-A4 an anode.

FIG. 6 illustrates an example of baroreflex response results for testing various bipolar stimulation configuration using electrode E4 as an anode and testing each of electrodes E1-E3 as a cathode. The tested configuration uses electrode E4 as an anode (+), and may use any one of electrodes 1, 2, 3 as a cathode. The cathode may also referred to as a return electrode (−). A table of data may be recorded. For example, the amplitude (e.g. 3 mA) of the stimulation may be provided, as well as the change in the mean arterial pressure (MAP). In some embodiments, the impedance (z) may also be recorded.

FIG. 7 illustrates an example of baroreflex response results for testing various bipolar stimulation configuration using each of electrodes C1-C4 as a cathode and using each one of electrodes A1-A4 an anode. The cathode may also referred to as a return electrode (−). A table of data may be recorded. For example, the columns may be labeled C1-C4, and the rows may be labeled A1-A4. The change in the mean arterial pressure (MAP) may be recorded for each combination of the cathode and anode.

Figure 8B:
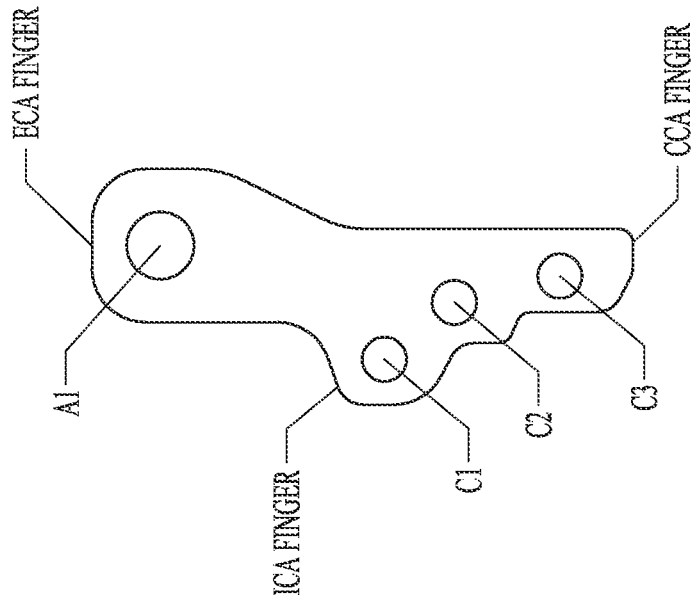
FIGS. 8A-8E illustrate various electrode patch examples configured for attachment over the carotid sinus.
Figure 8A:
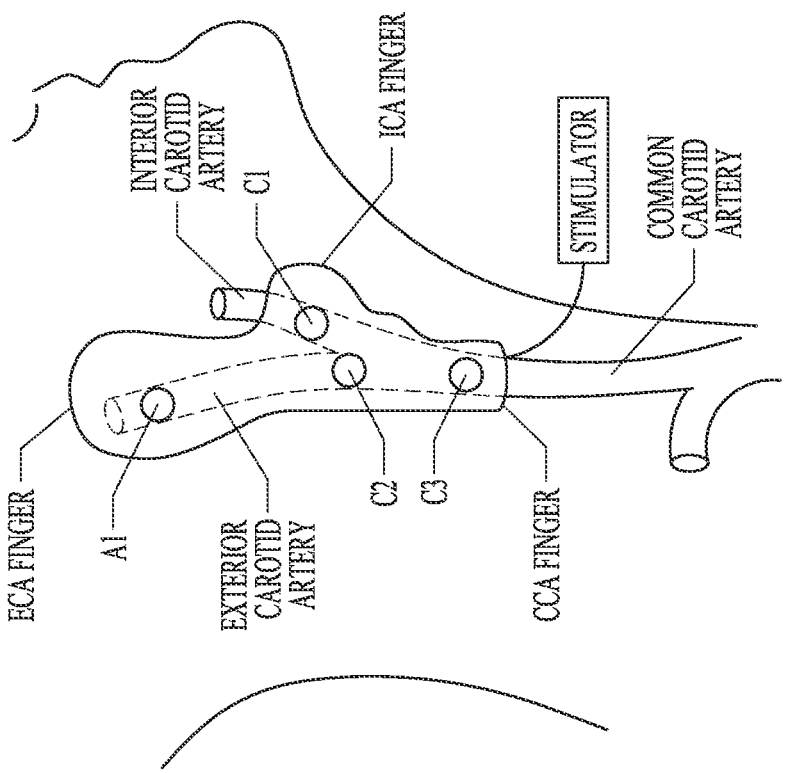
Figure 8E:
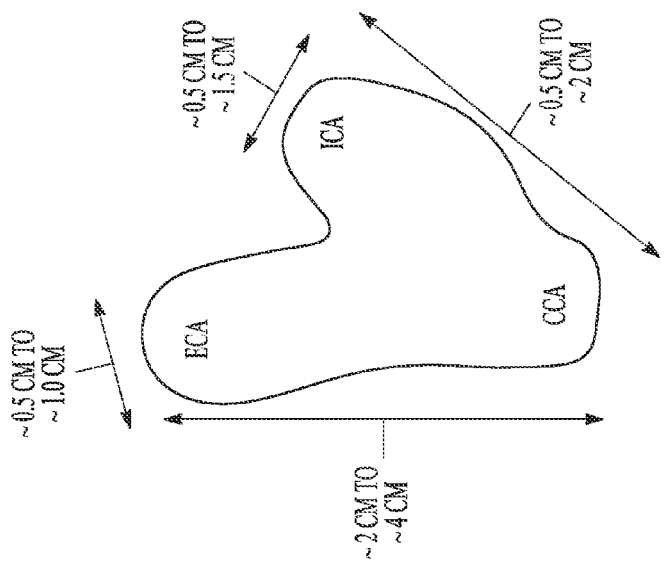
Figure 8D:
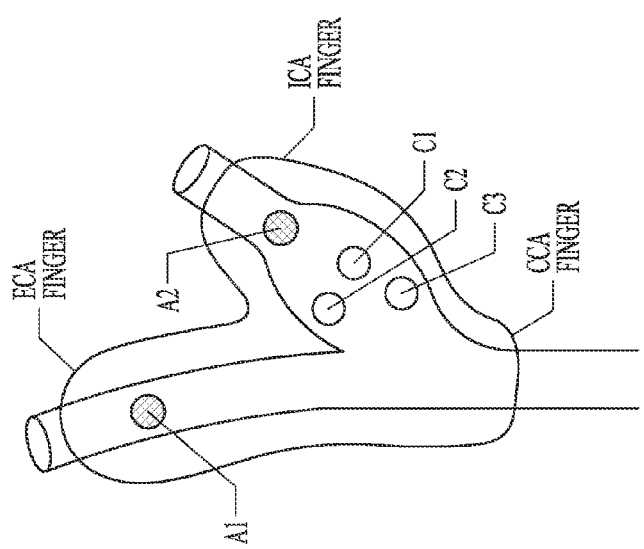
Figure 8C:
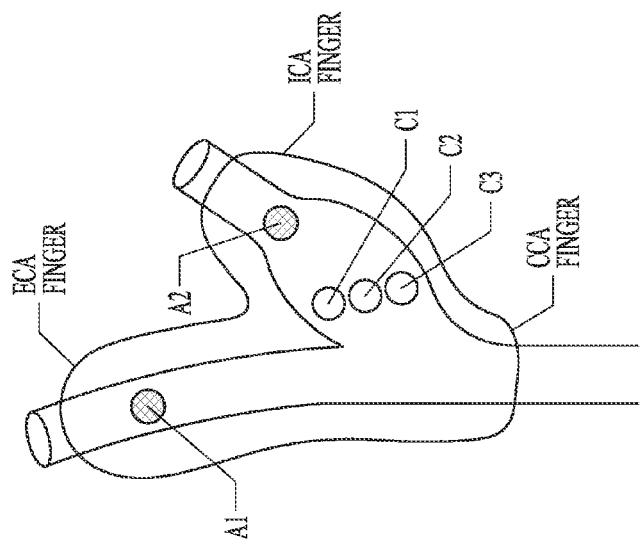

FIGS. 8A-8E illustrate various electrode patch examples configured for attachment over the carotid sinus. The patch may have protrusions, which may be referred to as fingers. A CCA finger runs along the common carotid artery, an ICA finger runs along the interior carotid artery, and the ECA finger runs along the exterior carotid artery. The region in between the fingers may be referred to as a bifurcation region. FIGS. 8A-8B illustrate one example, which has an anode and three cathodes. When placed on the tissue, the anode (A1) is positioned over the exterior carotid artery (ECA), and three cathodes (C1, C2, C3) are positioned to place an electrode on the interior carotid artery (ICA), the common carotid artery (CCA), and the bifurcation. In other words, the ECA finger has an anode electrode, and each of the ICA finger, the bifurcation region, and the CCA finger has a cathode. FIGS. 8C-8D illustrates an electrode patch example with a cathode group positioned on the exterior carotid artery. For example, the cathode grouping may be in a generally linear arrangement as illustrated in FIG. 8C, and some cathode groupings are non-linear as illustrated in FIG. 8D. Some embodiments provide an anode on the ECA finger, some embodiments provide an anode on the ICA finger, and some embodiments provide both an anode on the ICA finger and another anode on the ECA finger. FIG. 8E illustrates an example of a patch, similar to that which is illustrated in FIG. 8D. Various electrode patch embodiments may have dimensions within a range as illustrated in FIG. 8E. For example, the length of the patch from the CCA edge to the ECA edge may be within a range of about 2 cm to about 4 cm, and the length of the ICA finger of the patch may be within a range of about 0.5 cm to about 2 cm. The width of the ECA finger may be about 0.5 cm to about 1 cm, the width of the ICA finger may be about 0.5 cm to about 1.5 cm. In some embodiments, the distance between cathodes may be within a range of about 0.5 mm to 2 mm edge to edge.

Figure 9:
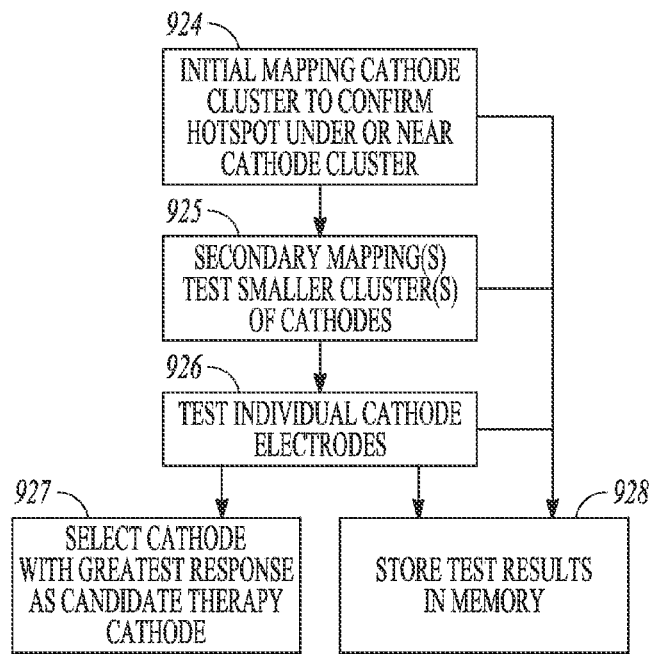
FIG. 9 illustrates an embodiment of a method for using electrode clustering to map a baroreceptor region.

FIG. 9 illustrates an embodiment of a method for using electrode clustering to map a baroreceptor region. At 924, a cluster of cathodes may be initially mapped to confirm that a baroreceptor hotspot is under or near the cluster of cathodes. These test results may be stored in memory 928. If a baroreceptor hotspot is not found, then the patch may be repositioned and the initial mapping performed again. The initial mapping may be performed before the patch is sutured, or may be performed before the patch is completely sutured in place so that the patch may be moved if necessary to obtain a positive initial mapping. At 925, one or more secondary mappings may be performed to test smaller clusters of cathodes for the baroreceptor hotspot. These smaller clusters may be referred to as cluster subsets. Multiple subsets may be tested, as well as subsets of subsets. These test results may be stored in memory, as illustrated at 928. At 926 individual cathode electrodes may be tested to determine the cathode(s) near a baroreceptor hotspot. The mapping process may include intelligence, such that only those individual cathodes within the subset(s) where a baroreceptor hotspot was found may be mapped. These test results may be stored in memory 928, as illustrated at 928. At 927 a cathode with the greatest response may be tested as a candidate therapy cathode.

Figure 10:
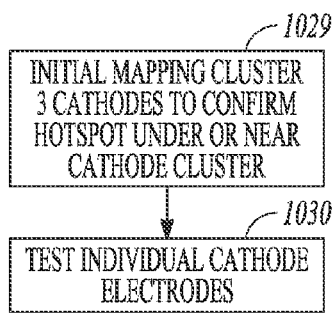
FIG. 10 illustrates an embodiment of a method for using electrode clustering, such as may use the electrode patch illustrated in FIGS. 8A-8D, to map a baroreceptor region.

FIG. 10 illustrates an embodiment of a method for using electrode clustering, such as may use the electrode patch illustrated in FIGS. 8A-8D, to map a baroreceptor region. At 1029 three cathodes are clustered together and an initial mapping is performed on the cluster to confirm that a baroreceptor hotspot is under or near the cathode cluster. If a baroreceptor hotspot is not found, then the patch may be repositioned and the cluster of cathodes can be again tested. If a baroreceptor hotspot is found, then the individual cathode electrodes may be tested at 1030 to determine which cathode(s) or over or near the baroreceptor hotspot. These cathode(s) can be used as the candidate therapy cathode(s).

Figure 11:
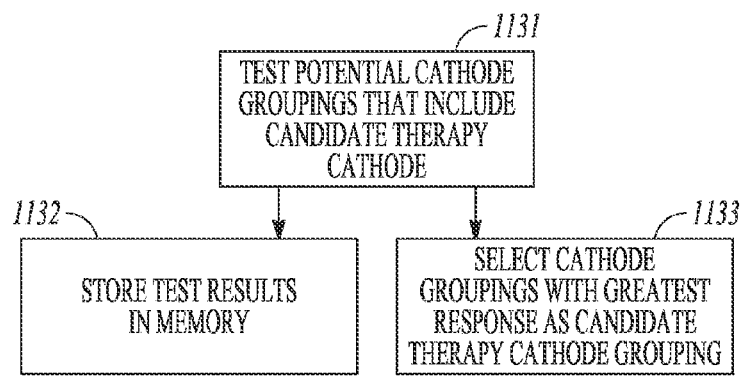
FIG. 11 illustrates an embodiment of a method for mapping a baroreceptor region that finds a candidate therapy cathode with the greatest baroreflex response, and then tests clusters that include additional cathodes with the candidate therapy cathode to test for an improved baroreflex response.

FIG. 11 illustrates an embodiment of a method for mapping a baroreceptor region that finds a candidate therapy cathode with the greatest baroreflex response, and then tests clusters that include additional cathodes with the candidate therapy cathode to test for an improved baroreflex response. This method may be performed after a candidate therapy cathode has been found, such as may be found using the methods illustrated FIG. 9 or 10. The candidate therapy electrode may be combined with one or more additional cathodes to further improve the baroreflex response to the stimulation. Thus, at 1131 one or more cathode groupings that include the candidate therapy electrode are tested, and the test results may be stored in memory as illustrated at 1132. At 1133 the cathode groupings with the greatest baroreflex response may be selected as a candidate therapy cathode grouping. The candidate therapy cathode grouping may be further tested or evaluated to confirm that undesired stimulation of other tissue (e.g. muscle) is not present, and/or that the appropriate safety margin is maintained.

Figure 12:
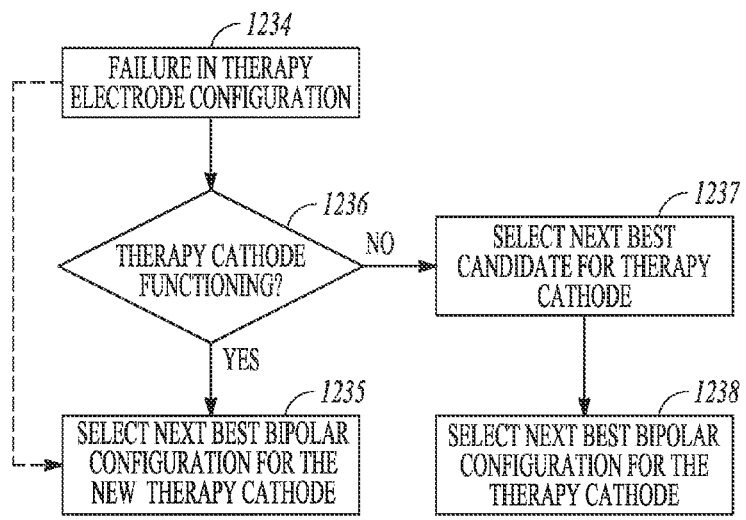
FIG. 12 illustrates a method fir responding to a failure in a therapy electrode configuration.

FIG. 12 illustrates a method for responding to a failure in a therapy electrode configuration. At 1234, a failure in a therapy electrode configuration occurs, this failure may be detected by the stimulation system. The failure may be attributable to hardware or firmware, or may be attributable to changes in the patient physiology. The failure may cause the therapy to be less effective, or may prevent the therapy from being delivered. In some embodiments the next best bipolar configuration (anode(s) and cathode(s)) may be selected for the therapy cathode as illustrated at 1235. The information used to select the next best configuration may be derived from the results from previous mapping tests, and this information may be stored with the implantable system or with an external device. Some embodiments may determine of the therapy cathode is still functioning, as illustrated at 1236. If the therapy cathode is functioning, then the next best anode/cathode configuration may be selected for the therapy cathode as illustrated at 1235. If the therapy cathode is not functioning, then the next best candidate for the therapy cathode may be selected at 1237. The next best bipolar configuration is selected using this new therapy cathode 1238.

Figure 13A:
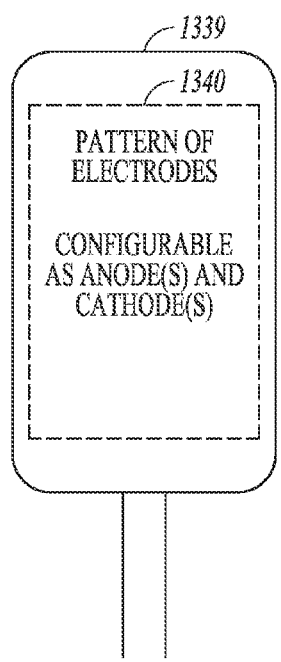
FIGS. 13A-13C illustrate examples of multi-electrode leads for use in mapping a baroreceptor region.
Figure 13B:
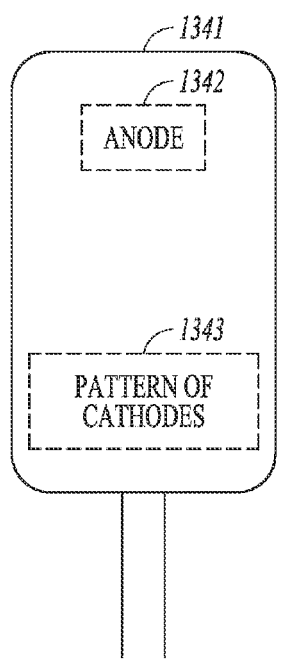
Figure 13C:
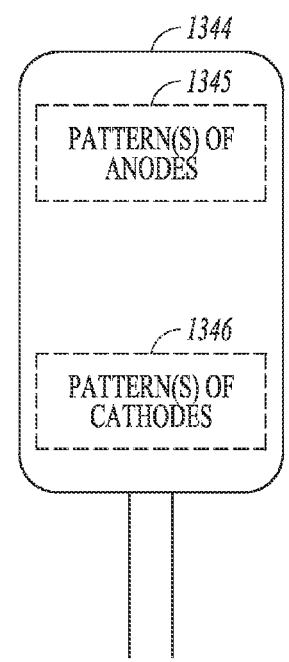

FIGS. 13A-13C illustrate examples of multi-electrode leads for use in mapping a baroreceptor region. These examples illustrate that the multi-electrode lead may include a variety of patterns of electrodes. FIG. 13A illustrates a lead 1339 with one pattern 1340 of electrodes. The lead is configured to use at least one of the electrodes in the pattern as an anode and is capable of using any one or more of the electrodes in the pattern as a cathode. An electrode within the pattern may be configured to be used as either an anode or a cathode. FIG. 13B illustrates a lead 1341 with an anode 1342 and with a pattern of potential cathodes 1343. The lead may be configured to use the anode and any one or more of the electrodes in the pattern of cathodes to provide bipolar stimulation. FIG. 13C illustrates a lead 1344 with a pattern of potential anodes 1345 and a pattern of potential cathodes 1346. The lead may be configured to use any one or any combination of the potential anodes as an anode for bipolar stimulation, and to use any one or any combination of the potential cathodes as a cathode for the bipolar stimulation. There may be more than one pattern of potential anodes, and more than one pattern of potential cathodes. The pattern may be two electrodes at desired locations. For example, FIG. 8D illustrate a pattern of two potential anodes (A1 and A2).

Figure 14:
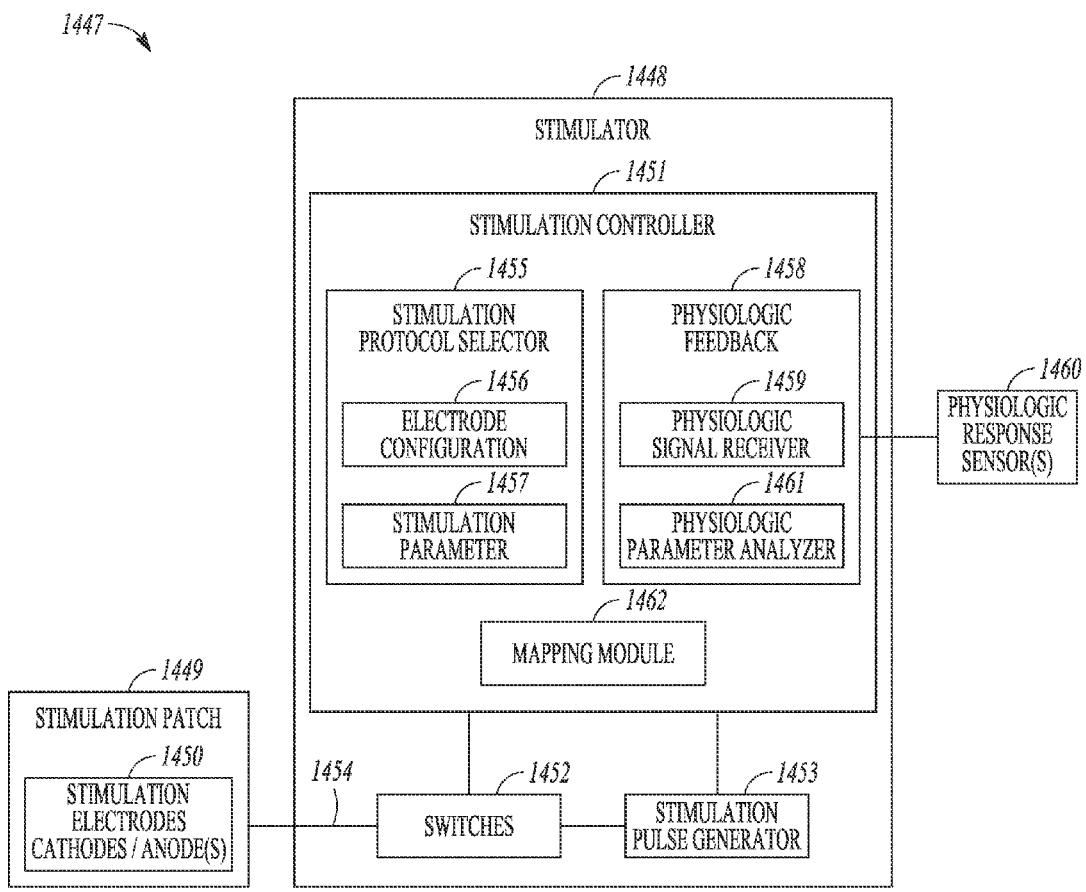
FIG. 14 illustrates an example of a system for mapping a baroreflex system.

FIG. 14 illustrates an example of a system for mapping a baroreflex system. The illustrated system 1447 includes a stimulator 1448 and a stimulation patch 1449 with stimulation electrodes 1450 that may be configured for delivering bipolar stimulation. The illustrated stimulator 1448 may include a stimulation controller 1451, a switch module 1452, and a stimulation pulse generator 1453. The switches 1452 selectively connect lead conductors 1454 to connect stimulation electrodes 1450 to the pulse generator 1453. The illustrated controller 1451 may include a stimulation protocol selector 1455. The stimulation protocol selector 1455 may include an electrode configuration selector 1456, which may work with the switch module 1452 to control switching, similar to the switching mechanism 204 in FIG. 2. The stimulation protocol selector 1455 may also include a stimulation parameter selector which may work with the stimulation pulse generator to control the parameters of the neural stimulation. Examples of such parameters include the amplitude, pulse width, pulse frequency, burst duration, burst frequency, or other start/stop parameters of the stimulation. The controller may also include a physiologic feedback module 1458. The physiologic feedback module 1458 may include a physiologic signal receiver 1459 to receive signal(s) from physiologic response sensor(s) 1460, and a physiologic parameter analyzer 1461 configured to analyze the received signal to provide feedback used to control the stimulation. The stimulation controller 1451 may also include a mapping module 1462 used to control a mapping process and store the results from the mapping.

Figure 15:
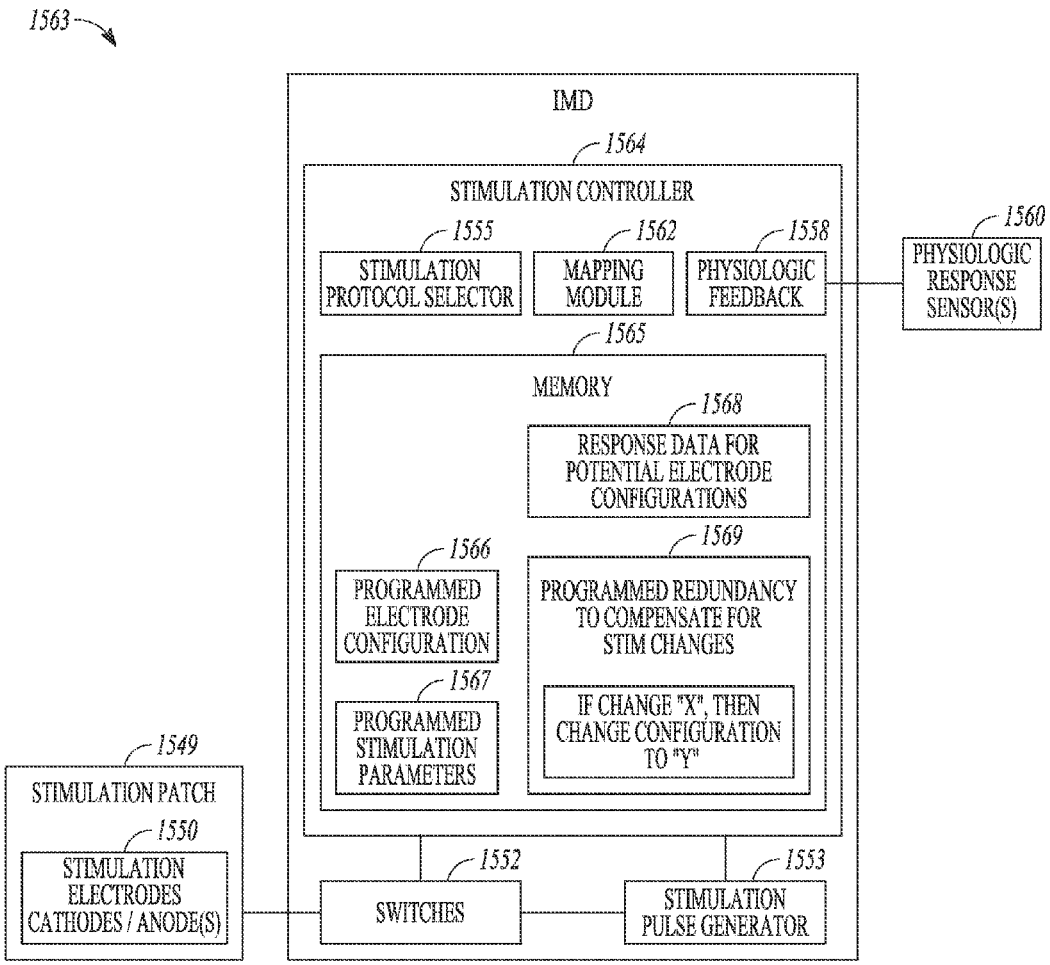
FIG. 15 illustrates an example of a system that includes an implantable device with programmed redundancy determined using baroreceptor mapping data.
Figure 16A:
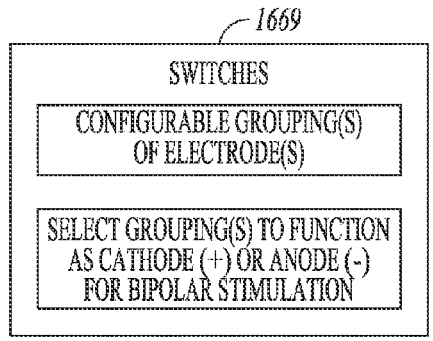
FIGS. 16A-16D illustrate examples of switch mechanisms for grouping electrodes.
Figure 16B:
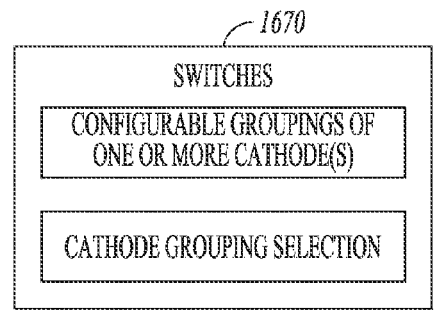
Figure 16C:
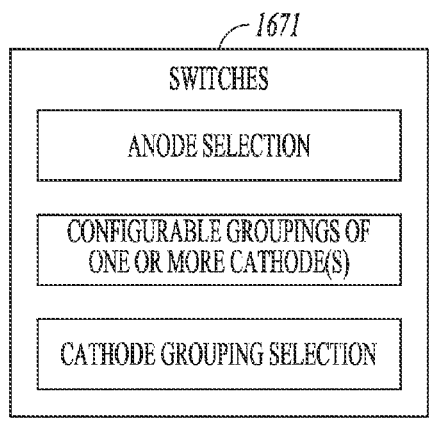
Figure 16D:
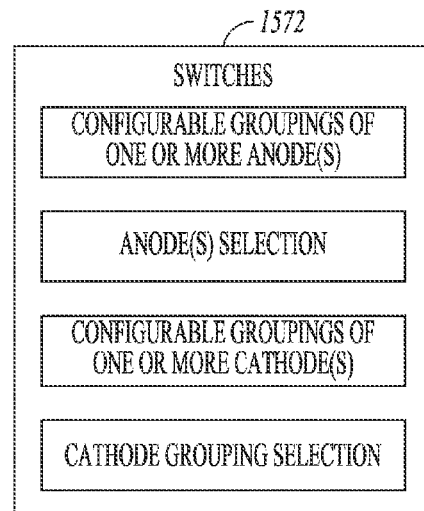

FIG. 15 illustrates an example of a system 1563 that includes an implantable device (IMD) with programmed redundancy determined using baroreceptor mapping data. The system 1563 may include a stimulation patch 1549 with stimulation electrodes, similar to the patch 1449 and electrodes 1450 in FIG. 14. The system 1563 may also include a switch module 1552, stimulation pulse generator 1553, and a stimulation controller 1564 with a stimulation protocol selector 1555, similar to the switch module 1452, pulse generator 1453, protocol selector 1452 in FIG. 14. The system 1563 may also include a physiologic feedback 1558, physiologic response sensor(s) 1560 and mapping module 1562 similar to feedback 1458, sensor(s) 1460 and mapping module 1462 in FIG. 14. The illustrated controller 1564 includes memory 1565 with a programmed electrode configuration 1566 and programmed stimulation parameters 1567 for delivering a therapy. The memory 1565 may also include response data for potential electrode configurations 1568 and programmed redundancy to compensate for stimulation changes 1569. Thus, the system may be configured to respond to a change by changing the bipolar stimulation configuration.

FIGS. 16A-16D illustrate examples of switch mechanisms for grouping electrodes. These switching mechanism may correspond to switching mechanism 204 in FIG. 2, a combination of switches 1452 and electrode configuration selector 1456 in FIG. 14 or a combination of switches 1552 and selector 1555 in FIG. 15. The switch mechanism 1669 in FIG. 16A may include configurable grouping(s) of electrode(s), and may be configured to select grouping(s) to function as a cathode or anode through which to deliver bipolar stimulation. The groupings may be referred to as clusters. The switch mechanism 1670 in FIG. 16B may include configurable groupings of one or more cathode(s), and may be configured to select a grouping of cathodes through which to deliver bipolar stimulation. The switch mechanism 1671 in FIG. 16C may include configurable groupings of one or more cathode(s), and may be configured to select an anode and to select a cathode grouping of one or more cathodes. The switch mechanism 1672 in FIG. 16D may include configurable groupings of anode(s) and configurable groupings of cathode(s), and may be configured to select anode(s) and a grouping of cathodes through which to deliver bipolar stimulation.

Figure 17:
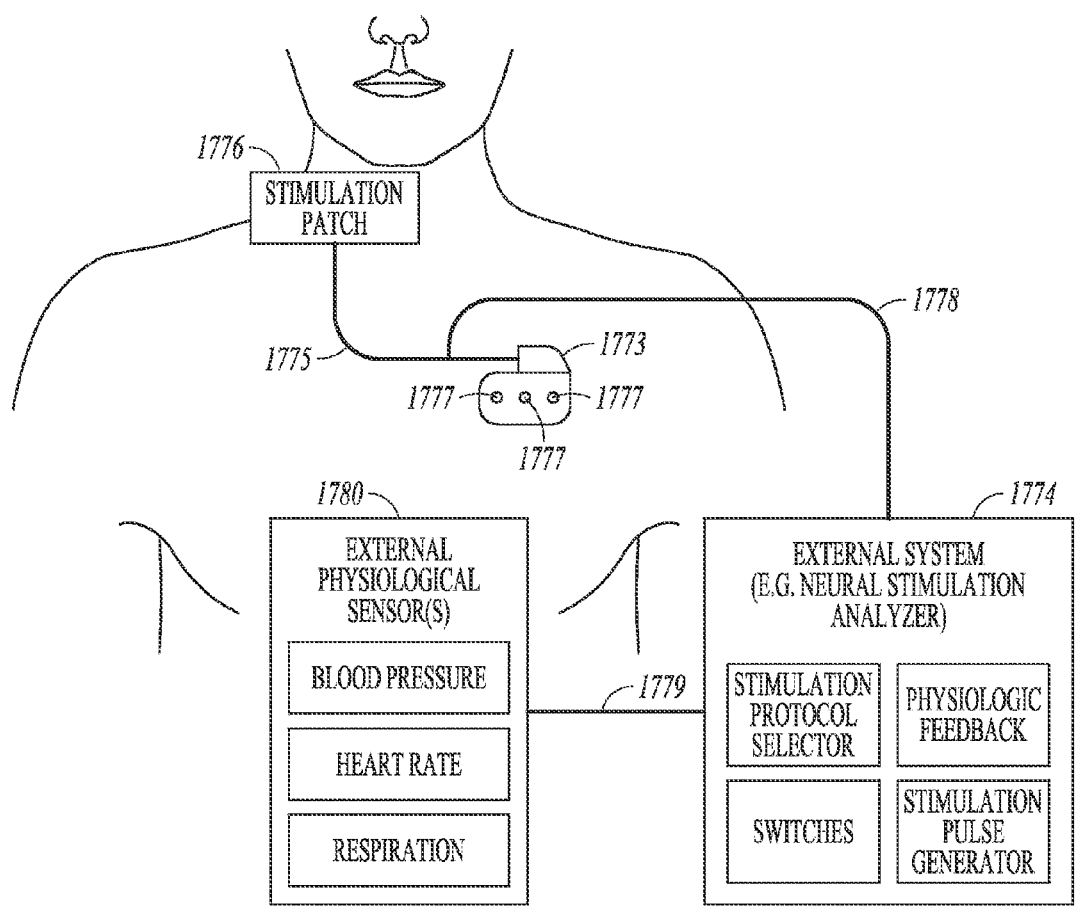
FIG. 17 illustrates an implantable neural stimulator and an embodiment of an external system such as a neural stimulation system analyzer.

FIG. 17 illustrates an implantable neural stimulator 1773 and an embodiment of an external system 1774 such as a neural stimulation system analyzer. The illustrated implantable neural stimulator 1773 is placed subcutaneously or submuscularly in a patient's chest with a lead 1775 positioned to stimulate baroreceptors in a carotid sinus region. The lead includes a stimulation patch 1776 with a plurality of electrodes. The illustrated system provides a lead to the right carotid sinus region. The lead could be routed to the left carotid sinus region. Some embodiments may use leads to stimulate both the left and right carotid sinus regions. The neural stimulator may include leadless ECG electrodes 1777 on the housing of the device, which are capable of being used to detect heart rate, for example, to provide feedback for the neural stimulation therapy. At the time of the implantation of the neural stimulator, a test lead cable 1778 may be temporarily connected to the implanted neural stimulation lead 1776 to enable the analyzer to determine an appropriate placement of the lead, and verify the integrity of the stimulation path within the lead. Sensor cable(s) 1779 connect the external system 1774 to external physiology sensors 1780. These sensor(s) are used by the analyzer to detect a baroreflex response. For example, heart rate, blood pressure, or respiration may be sensed to detect a baroreflex response. The external system 1774 may include a switch module, stimulation protocol selector, a stimulation pulse generator, and a physiologic feedback, similar to the systems discussed in FIGS. 14 and 15.

Figure 18:
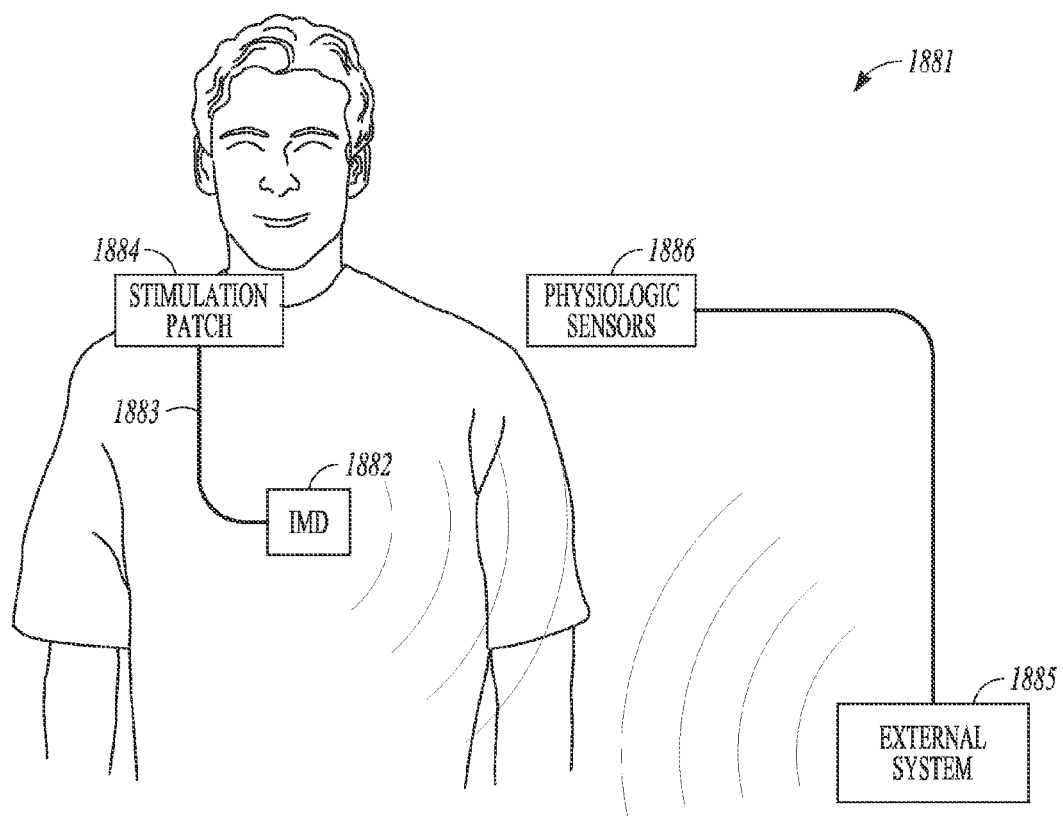
FIG. 18 illustrates a system embodiment fir mapping a baroreflex region which uses an external system to communicate with an implantable device to control the mapping process using the implantable device to deliver bipolar stimulation.

FIG. 18 illustrates a system embodiment 1881 for mapping a baroreflex region which uses an external system to communicate with an implantable device to control the mapping process using the implantable device to deliver bipolar stimulation. An implantable medical device 1882 is configured to stimulate a baroreceptor region using a lead 1883 with a stimulation patch 1884. An external system 1885 is configured to wirelessly communicate with the IMD 1882. One example of an external device is a programmer. The external system 1885 can be used to control the mapping process discussed herein. For example, the external system 1885 can instruct the IMD 1882 to deliver bipolar stimulation using various bipolar stimulation configurations, and the external system 1885 can use physiologic sensors 1886 to monitor the baroreflex response to the bipolar stimulation. The external system 1885 can record the mapping results, or a portion thereof, for the available bipolar stimulation configurations in external memory of the external system, and/or record the mapping results, or a portion thereof, for the available bipolar stimulation configurations in the IMD 1882. In some embodiment, for example, the external system 1885 uses mapping results to program redundancy in the IMD 1882. The programmed redundancy identifies a different bipolar electrode configuration for use if the current bipolar stimulation configuration fails.

Various embodiments have been described above for mapping a baroreceptor region. Some examples are claimed below.

Various embodiments have been described for stimulating baroreceptors in a carotid sinus region. Some of these examples are provided below.

A first example provides a system for stimulating baroreceptors carotid sinus region of a patient, comprising: a lead with a plurality of conductors and a plurality of electrodes, wherein each of the plurality of electrodes is connected to a respective one of the plurality of conductors, wherein the plurality of electrodes are configured to be laterally attached to tissue in the carotid sinus region near a laterally-exposed bifurcation of an interior carotid artery and exterior carotid artery off of a common carotid artery.

A second example provides the system of the first example, further comprising a patch configured to be laterally attached to the tissue in the carotid sinus region near the laterally-exposed bifurcation of the interior carotid artery and exterior carotid artery off of the common carotid artery, wherein the plurality of electrodes are attached to the patch.

A third example provides the system of example 2, wherein the patch has a periphery and a suture margin around the periphery.

A fourth example provides the system of example 2, wherein the plurality of electrodes includes a first electrode, a second electrode, a third electrode and a fourth electrode arranged on the patch in a pattern, wherein the pattern of electrodes on the patch is configured to position, when the patch is laterally attached to the tissue in the carotid sinus region, the first electrode on or near the exterior carotid artery, and the second, third and fourth electrodes on or near the interior carotid artery proximate to the bifurcation.

A fifth example provides the system of example 4, wherein the system is configured to use the first electrode as an anode electrode, and to use the second, third and fourth electrodes as cathode electrodes.

A sixth example provides the system of example 5, wherein the anode electrode has a surface area larger than each one of the cathode electrodes.

A seventh example provides the system of example 6, wherein the patch has a periphery including a suture margin around the periphery, the periphery of the patch having an irregular shape in which at least a portion of the suture margin along the periphery is adjacent to the second, third and fourth electrodes.

An eighth example provides the system of example 7, wherein the irregular shape generally corresponds to the orientations of the common carotid artery, the interior carotid artery, and the exterior carotid artery, thereby promoting a less invasive surgical procedure to laterally expose the carotid arteries and laterally attach the patch to the tissue in the carotid sinus.

A ninth example provides the system of example 1, wherein each of the plurality of electrodes have a generally circular footprint.

A tenth example provides the system of example 1, wherein the plurality of electrodes includes a first pattern of electrodes and at least one other electrode, and the system is configured to use any one or more of the electrodes in the first pattern as a cathode and use the at least one other electrode as an anode.

An eleventh example provides the system of example 1, wherein the plurality of electrodes includes a first pattern of electrodes and a second pattern of electrodes, and the system is configured to use any one or more of the electrodes in the first pattern as a cathode and use any one or more of the electrodes in the second pattern as an anode.

A twelfth example provides the system of example 1, further comprising a switching mechanism configured to connect one or more of the plurality of conductors to configure one or more of the electrodes as an anode, and configured to connect at least one of the plurality of conductors to configure another one or more of the electrodes as a cathode.

A thirteenth example provides the system of example 12, wherein the switching mechanism is configured to connect a first set of the conductors together to form a first electrode cluster and to disconnect the first set of the conductors to disassemble the first electrode cluster.

A fourteenth example provides the system of example 13, wherein the switching mechanism is configured to connect a second set of conductors together to form a second electrode cluster and to disconnect the second set of the conductors to disassemble the second electrode cluster, wherein the first set of conductors is a subset of the second set of conductors and the first electrode cluster is a subset of the second electrode cluster.

A fifteenth example provides the system of example 13, wherein the switching mechanism is configured to connect conductors together to form another electrode cluster that includes at least one but less than all of the electrodes within the first electrode cluster and that also includes at least one other electrode.

A sixteenth example provides the system of example 13, wherein the switching mechanism is configured to connect conductors together to form another electrode cluster with electrodes exclusive of those electrodes within the first electrode cluster.

A seventeenth example provides a system for stimulating a carotid sinus region of a patient, comprising:

a lead with a plurality of conductors and a plurality of electrodes, wherein each of the plurality of electrodes is connected to a respective one of the plurality of conductors, wherein the plurality of electrodes are configured to be laterally attached to tissue in the carotid sinus region near a laterally-exposed bifurcation of an interior carotid artery and exterior carotid artery off of a common carotid artery;

a patch configured to be laterally attached to the tissue in the carotid sinus region near the laterally-exposed bifurcation of the interior carotid artery and exterior carotid artery off of the common carotid artery, wherein the plurality of electrodes are attached to the patch, wherein the patch has a periphery including a suture margin for suturing the patch to tissue near the laterally-exposed bifurcation;

the plurality of electrodes include a first electrode, a second electrode, a third electrode and a fourth electrode arranged on the patch in a pattern, wherein the pattern of electrodes on the patch is configured to position, when the patch is attached to the tissue in the carotid sinus region, the first electrode on or near the interior carotid artery, the second electrode on or near the common carotid artery, the third electrode on or near the bifurcation, and the fourth electrode on or near the exterior carotid artery.

An eighteenth example provides the system of example 17, further comprising a switching mechanism and a pulse generator, wherein the switching module is configured to connect the first electrode to the pulse generator as an anode, and configured to cluster the second, third and fourth electrodes together and to the pulse generator to function as a cathode cluster, and wherein the switching module is configured to disassemble the cathode cluster and selectively connect any one of the second, third or fourth electrode to the pulse generator as a cathode.

A nineteenth example provides a method for implanting a lead to stimulate baroreceptors in the carotid sinus region, comprising:

exposing a bifurcation of a common carotid artery into an interior carotid artery and exterior carotid artery, wherein exposing the bifurcation is generally limited to a lateral exposure of the bifurcation; and suturing a patch of electrodes on tissue in the carotid sinus region to position the first electrode on or near the interior carotid artery, the second electrode on or near the common carotid artery, the third electrode on or near the bifurcation, and the fourth electrode on or near the exterior carotid artery;

A twentieth example provides the method of example 19, further comprising:

mapping a baroreceptor region in the carotid sinus region after the patch is sutured on the tissue, including:
  delivering bipolar stimulation using the first electrode as the anode and second electrode as a cathode, monitoring for a corresponding baroreflex response and using an accelerometer to sense for undesired tissue capture;
  delivering bipolar stimulation using the first electrode as the anode and third electrode as the cathode, monitoring for a corresponding baroreflex response and using the accelerometer to sense for undesired tissue capture;
  delivering bipolar stimulation using the first electrode as the anode and the fourth electrode as the cathode, monitoring for a corresponding baroreflex response and using the accelerometer to sense for undesired tissue capture; and
  selecting at least one of the second, third or fourth electrodes for use as the cathode to deliver therapy based on the monitored baroreflex response and results from the accelerometer sensing.

The above detailed description is intended to be illustrative, and not restrictive. Other embodiments will be apparent to those of ordinary skills in the art upon reading and understanding the above description. The scope of the disclosure should, therefore, be determined with references to the appended claims, along with the full scope of equivalents to which such claims are entitled.

What is claimed is:

1. A method, comprising:
  placing a set of stimulation electrodes on tissue containing a baroreceptor region;
  automatically mapping the baroreceptor region using a controller and at least one physiologic response sensor, including:
    testing bipolar configurations of the electrodes, each of the bipolar configurations of the electrodes including at least one of the electrodes configured to function as an anode and at least one other of the electrodes configured to function as a cathode, wherein testing the bipolar configurations includes stimulating the tissue using each of the bipolar configurations;
    for each of the tested bipolar configurations monitoring at least one physiological parameter for a baroreflex response to stimulation of the tissue; and
    recording the baroreflex response for each of the tested bipolar configurations.

2. The method of claim 1, further comprising selecting a candidate therapy bipolar configuration, wherein the candidate therapy bipolar configuration is the tested bipolar configuration with a greatest baroreflex response to the stimulation of the tissue.

3. The method of claim 2, further comprising identifying a candidate therapy cathode for the candidate therapy bipolar configuration that provides a large baroreflex response to the stimulation of the tissue, wherein the large baroreflex response indicates that the candidate therapy cathode is proximate to a baroreceptor hotspot.

4. The method of claim 3, further comprising grouping the candidate therapy cathode with at least one adjacent cathode to provide a cathode cluster, stimulating the tissue using the cathode cluster, and monitoring for an increased baroreflex response when stimulating using the cathode cluster.

5. The method of claim 2, further comprising using the recorded baroreflex response to identify a backup candidate therapy bipolar configuration for use in response to a failure in the candidate therapy bipolar configuration.

6. The method of claim 1, wherein the at least one physiological parameter includes at least one of a heart rate parameter, a blood pressure parameter, or a respiration parameter.

7. The method of claim 1, wherein placing the set of stimulation electrodes includes suturing a patch over the tissue, the patch including the set of stimulation electrodes.

8. The method of claim 1, further comprising monitoring for undesired capture of adjacent tissue while testing each of the tested bipolar configurations, and identifying a candidate therapy bipolar configuration based on the monitored baroreflex responses and monitored undesired capture of adjacent tissue.

9. A method, comprising:
  placing a set of stimulation electrodes on tissue containing a baroreceptor region; and
  automatically mapping the baroreceptor region using a controller and at least one physiologic response sensor, including:
    mapping one or more cathode clusters to confirm at least one of the cathode cluster is proximate to a baroreceptor hotspot, wherein each of the cathode clusters includes three or more of the stimulation electrodes connected to function as a cathode and wherein at least one other of the stimulation electrodes is connected to function as an anode;
    for each cathode cluster confirmed to be proximate to the baroreceptor hotspot, conducting a secondary mapping to test at least two smaller cathode clusters to confirm at least one of the smaller cathode clusters is proximate to the baroreceptor hotspot;
    for each smaller cathode cluster confirmed to be proximate to the baroreceptor hotspot, mapping individual cathode electrodes within the smaller cathode cluster to confirm at least one of the individual cathode electrodes is proximate to the baroreceptor hotspot.

10. The method of claim 9, further comprising:
  for each smaller cathode cluster confirmed to be proximate to the baroreceptor hotspot, conducting another mapping of at least two subsets of the smaller cathode cluster to confirm at least one of the subsets is proximate to the baroreceptor hotspot, wherein mapping individual cathode electrodes within the smaller cathode cluster includes mapping individual cathode electrodes within one or more subsets confirmed to be proximate to the baroreceptor hotspot.

11. The method of claim 9, wherein mapping includes:
testing at least one bipolar configuration of the electrodes;
for each of the tested bipolar configurations monitoring at least one physiological parameter for a baroreflex response to stimulation of the tissue; and
recording the baroreflex response for each of the tested bipolar configurations.

12. The method of claim 9, further comprising selecting a candidate therapy electrode from the at least one of the individual cathode electrodes confirmed to be proximate to the baroreceptor hotspot.

13. The method of claim 12, further comprising grouping the candidate therapy cathode with at least one adjacent cathode to provide a cathode cluster, stimulating the tissue using the cathode cluster, and monitoring for an increased baroreflex response when stimulating using the cathode.

14. The method of claim 9, wherein placing the set of stimulation electrodes includes suturing a patch over the tissue, the patch including the set of stimulation electrodes.

15. A system for mapping a baroreceptor region, comprising:
stimulation electrodes for placement on tissue containing the baroreceptor region;
a stimulator, including a stimulation controller, a pulse generator, and switches, wherein the stimulation controller and switches are configured to connect different combination of the stimulation electrodes to the pulse generator to deliver bipolar stimulation of the tissue;
at least one physiologic response sensor configured to sense a physiologic response to stimulation of the tissue;
the controller including a stimulation protocol selector configured to select electrode configurations for testing, including control the switches to connect the pulse generator to the stimulation electrodes to provide selected electrode configurations for testing;
the controller including a physiologic feedback module to receive a signal from the at least one sensor, and a physiologic parameter analyzer configured to monitor a baroreflex response; and
the controller is configured to use the stimulation protocol selector and the physiologic feedback module to map the baroreceptor region, including:
stimulate the tissue using bipolar configurations of the electrodes to test the bipolar configurations, each of the bipolar configurations of the electrodes including at least one of the electrodes functioning as an anode and at least one other of the electrodes functioning as a cathode;
for each of the tested bipolar configurations monitor at least one physiological parameter for a baroreflex response to stimulation of the tissue; and
record the baroreflex response for each of the tested bipolar configurations.

16. The system of claim 15, further comprising a patch, wherein the stimulation electrodes are connected to the patch and the patch is configured to be sutured to the tissue.

17. The system of claim 15, wherein the controller is configured to select a candidate therapy cathode for the candidate therapy bipolar configuration that provides a large baroreflex response to the stimulation of the tissue, wherein the large baroreflex response indicates that the candidate therapy cathode is proximate to a baroreceptor hotspot.

18. The system of claim 17, wherein to map the baroreceptor region, the controller is configured to group the candidate therapy cathode with at least one adjacent cathode to provide a cathode cluster, stimulate the tissue using the cathode cluster, and monitor for an increased baroreflex response when stimulating using the cathode cluster.

19. The system of claim 17, wherein to map the baroreceptor region, the controller is configured identify a backup candidate therapy bipolar configuration using the recorded baroreflex response, the controller including programmed redundancy using the backup candidate therapy bipolar configuration to compensate for changes.

20. The system of claim 17, further comprising an accelerometer, wherein the controller is further configured to use the accelerometer to monitor for undesired capture of adjacent tissue while testing each of the tested bipolar configurations, and identify a candidate therapy bipolar configuration based on the recorded baroreflex responses and monitored undesired capture of adjacent tissue.

* * * * *